(12) United States Patent
Likova et al.

(10) Patent No.: US 10,722,150 B2
(45) Date of Patent: Jul. 28, 2020

(54) SYSTEM FOR TRAINING SPATIAL COGNITION, MEMORY AND SPATIOMOTOR COORDINATION THROUGH DRAWING

(71) Applicants: Lora T. Likova, Greenbrae, CA (US); Zlatko Kristev Minev, New Haven, CT (US)

(72) Inventors: Lora T. Likova, Greenbrae, CA (US); Zlatko Kristev Minev, New Haven, CT (US)

(*) Notice: Subject to any disclaimer, the term of this patent is extended or adjusted under 35 U.S.C. 154(b) by 0 days.

(21) Appl. No.: 16/429,012

(22) Filed: Jun. 2, 2019

(65) Prior Publication Data

US 2019/0282132 A1    Sep. 19, 2019

Related U.S. Application Data

(63) Continuation of application No. 15/650,971, filed on Jul. 16, 2017, now Pat. No. 10,307,087.

(51) Int. Cl.
| | | |
|---|---|---|
| *A61B 5/11* | (2006.01) | |
| *G09B 7/02* | (2006.01) | |
| *G09B 23/28* | (2006.01) | |
| *A61B 5/16* | (2006.01) | |
| *A61B 5/0484* | (2006.01) | |
| *G16H 50/30* | (2018.01) | |
| *G09B 19/00* | (2006.01) | |
| *G16H 20/70* | (2018.01) | |
| *G16H 40/60* | (2018.01) | |
| *G09B 21/00* | (2006.01) | |

(52) U.S. Cl.
CPC ........ *A61B 5/1124* (2013.01); *A61B 5/04842* (2013.01); *A61B 5/16* (2013.01); *G09B 7/02* (2013.01); *G09B 19/00* (2013.01); *G09B 23/28* (2013.01); *G16H 20/70* (2018.01); *G16H 40/60* (2018.01); *G16H 50/30* (2018.01); *G09B 21/003* (2013.01); *G09B 21/006* (2013.01)

(58) Field of Classification Search
CPC .......... A61H 5/00; A61B 3/032; A61B 3/024; A61B 3/0033; A61B 3/113
USPC ....................................................... 351/203
See application file for complete search history.

(56) References Cited

U.S. PATENT DOCUMENTS

| | | | | |
|---|---|---|---|---|
| 10,307,087 | B2* | 6/2019 | Likova | G16H 50/30 |
| 2006/0161218 | A1* | 7/2006 | Danilov | A61B 5/0492 |
| | | | | 607/45 |
| 2014/0045148 | A1* | 2/2014 | Ishiyama | G09B 11/00 |
| | | | | 434/85 |

* cited by examiner

*Primary Examiner* — Mohammed A Hasan
(74) *Attorney, Agent, or Firm* — Howard Cohen (57) ABSTRACT

A method for improving subject's spatial cognition and spatial memory includes presenting spatial information to the person through non-visual means, parcellating the image to enhance understanding of the nature and relationships of the image components to augment image memory, drawing the image, detecting and encoding the errors in the drawing, and providing interactive feedback based on the individual's drawing performance. The methodology includes audio-haptic feedback to present the spatial image information non-visually using an audible signal that varies as a function of the distance of the finger/stylus from the regions of a display that express the image features.

15 Claims, 4 Drawing Sheets

SYSTEM FOR TRAINING SPATIAL COGNITION, MEMORY AND SPATIOMOTOR COORDINATION THROUGH DRAWING

CROSS-REFERENCE TO RELATED APPLICATIONS

This application claims the filing date priority of corresponding Provisional Appl. No. 62/363,317, filed Jul. 17, 2016.

FEDERALLY SPONSORED RESEARCH

Not applicable.

SEQUENCE LISTING, ETC ON CD

Not applicable.

BACKGROUND OF THE INVENTION

Field of the Invention

This invention relates to the field of behavioral training of human beings for improved spatial and spatiomotor cognition and memory, and in particular to training those who are blind or have low vision as well as general training of fine spatiomotor and spatial memory skills in sighted people.

Challenges for the blind population: Humans are predominantly visual beings and the conventional electronic means for presenting of spatial information, such as drawings, graphs, pictures, etc. are visual, such as on flat display screens, which makes them inaccessible to the population of blind and severely low vision individuals. The conventional means thus cannot be directly used for any spatial cognition or spatiomotor non-visual training for those who are lacking vision. Currently, however, the population of blind or profoundly visually impaired people in the USA alone is about 1.3 million, and has a disturbingly high unemployment level of around 70% (American Foundation for the Blind Report, 2006). All activities of daily life, from pouring a glass of water, to manipulating office equipment, to navigating indoors or outdoors, depend on spatial cognition and visuomotor control. This is even more true for professional and workspace activities.

Description of Related Art

It is well known that graphical information is of key importance of both education and workplace communication—from simple graphs, charts, geometric figures to technical and artistic renderings. In the technical field of electronic presentation of non-visual spatial information, there is a lack of suitable devices. The standard tangible displays that are available are expensive, non-refreshable, and in particular are inconvenient for the automation of any training method, which requires refreshable media based on available computer systems.

BRIEF SUMMARY OF THE INVENTION

Importance of spatial cognition, memory and spatiomotor coordination & the need of training interventions for their enhancement:

All activities of daily life, from pouring a glass of water, to manipulating office equipment, to navigating indoors or outdoors, depend on spatial cognition and visuomotor control. Consequently, when vision is lost, its function must be replaced by mental representations (or mental 'maps') in non-visual spatial memory, and by the ability to use them effectively for spatiomotor control. Thus, scientific research into paradigmatically new and effective spatiomotor rehabilitation capitalizing on the supramodal nature of space and its mental representation becomes of crucial importance for quality of life, increased vocational opportunity, emotional valence, self-esteem and re-integration into society.

A key concept in this invention, underlying this approach to effective spatial cognition and spatio-motor rehabilitation is that the role of the eyes in these 'vision-dependent' functions, can be replaced by enhancing non-visual spatial cognition and memory to guide precise motor control.

One critical barrier faced by the traditional rehabilitation world is the typically piecemeal approach of distributed training over many separate daily tasks—a process that usually takes months or years of instruction. What is needed is an integrative rehabilitation approach to attack the core of the problem by addressing a wide-spectrum of components for spatial cognition and hand-movement control in a single, unified paradigm.

Clinical neurology and neuropsychology have long recognized drawing as a powerful multi-component tool for the diagnosis of spatiomotor and memory dysfunctions, such as constructional apraxia, Alzheimer's disease, and other brain pathologies. In particular, drawing performance is the basis for one of the most prevalent memory-deficit tests—the Clock Drawing Test, providing superior sensitivity, specificity and robustness. Drawing has the unique advantage of providing an explicit readout of wide-range components of neural functions from a single, unified assay.

Despite its advantages, the drawing paradigm has not been used in the blind population. Can the unique advantages of drawing be harnessed to provide the requisite wide-spectrum blindness rehabilitation tool within a single paradigm? It is the array of diverse functional subsystems involved in the drawing task that underlies its effectiveness as a diagnostic tool in neurology; the present invention builds on the same properties, but takes the complementary approach of using drawing as an instigator of positive change, operating simultaneously in many subsystems, such as non-visual working memory, spatial and spatiomotor cognition.

The blindness barrier. The inherently visual nature of drawing, however, is typically considered as an obvious barrier to its application to rehabilitation in blindness/profound visual impairment. We have developed, however, a powerful Cognitive-Kinesthetic Rehabilitation Method, based on a non-visual form of freehand drawing from memory of tactile models. Brain imaging studies have shown that this method can enhance working memory, and, in particular, the generation and maintenance of robust memory representations, which are of key importance for replacing the 'eye-hand' control lost in blindness by non-visual memory/hand control, and, hence, to fulfill the demand for wide-spectrum blindness rehabilitation through a single task.

This invention expands the concept of drawing as having the unique advantage of orchestrating a wide-range of neural functions, implying that drawing can be harnessed to provide the requisite wide-spectrum blindness rehabilitation tool within a single paradigm. This approach, the Cognitive-Kinesthetic Drawing Training Method, has fully supported our idea that drawing is not 'visual' art, but rather a spatial conceptual activity, in the amodal sense.

A key element of this invention is the recognition that memory-guided drawing, in particular, challenges the neural system to provide encoding, retrieval and effective 'projection' of memory representations of spatial relationships back onto some form of an internal high-resolution 'projection screen' in the brain, so as to provide the structural information to guide the spatial trajectory of the drawing-hand with the requisite precision. It thus closes the full processing 'loop' from perception through memory to precisely controlled motor action.

This novel training method is based on the spatiomotor task of drawing, because drawing—from artistic to technical—is a 'real-life' task that uniquely incorporates diverse aspects of perceptual, cognitive and motor skills, thus activating the full perception-cognition-action 'loop'. Drawing engages a wide range of spatial manipulation abilities (e.g., spatio-constructional decisions, coordinate transformations, geometric understanding and visualization, spatial analysis, memory), together with diverse mental representations of space, conceptual knowledge, motor planning and control mechanisms, working and long-term memory, attentional mechanisms, as well as empathy, emotions and forms of embodied cognition. For example, Likova, 2012 describes a brain imaging study that used, but did not reveal, aspects of the fundamental Cognitive-Kinesthetic Training Method referenced herein, suggesting that it is possible to use drawing for both training and studying training-based cross-modal plasticity in visual areas of the brain activated by non-visual tasks and throughout the whole brain. That study employed raised-line tactile models of objects and faces as shape inputs for experimental subjects to memorize and draw. However, that published study did not reveal any of the component procedures specified in the claims for the present inventions, which are described herein for the first time.

The present invention is a system for training a subject through drawing, comprising: providing a device for presenting spatial structure information to the person, provision for concurrent descriptive multi-level analysis of the segments or image content under the exploring hand(s) provided verbally, electronically or by human trainer, recording the subject's hand trajectory during exploration of spatial structure information for post-hoc analyses of dynamics of motor learning and during drawing of the spatial structure information for error analysis and error feedback and memory correction; detecting and encoding the errors in the drawing, and providing interactive feedback based on the individual's drawing performance at the respective level of the multi-level analysis. This sequence of operations implements a set of cognitive-kinesthetic training principles for the enhancement of spatial cognition, such as detailed non-visual perception, spatial memory and spatial analysis, and spatiomotor coordination through drawing either with or without vision, and providing error feedback to the subject of the nature of the drawing errors at several levels of analysis.

A novel aspect of the presentation component of the system is the concept of audio-haptic feedback for the presentation of non-visual spatial information through an auditory sound signal with an audio characteristic that varies as a function of the distance of the finger/stylus from the regions of the display that express the drawing features, so that the sound guides the exploring hand movements along the spatial-structure to perceive it without vision. This novel concept may be carried out on a wide variety of standard touch screen-based communication devices, such as a commercially available tablets, tablet computers or smart cell-phones. No special features or special equipment is required, since the audio-haptic implementation is embodied primarily in software. In this way, the system has full accessibility for blind, low vision and sighted users. In its automated manifestation, the system allows for independent usage by the training subject (i.e., with or without a trainer). It is cost-effective, based on an electronic app, easily downloadable, and refreshable. The app may be easily upgradable to any new refreshable non-visual technology presentation that becomes available. It is an open system thus allowing also to implement new principles/enhancement of drawing training as well or to serve educational purposes involving non-visual spatial presentations. The audio-haptic method allows for real-time automation of the non-visual presentation of the information independently to each individual, electronically implementing all levels of deconstruction, and linking a verbal description through an electronic voice to any part or segment of the image structure. This information presentation is implemented at each stage of the training process—from the exploration and memorization of the original image to the error feedback deriving from each drawing produced during the training process.

DETAILED DESCRIPTION OF THE INVENTION

The present invention generally comprises a system for training an individual to acquire enhanced spatial cognition, memory and spatiomotor skills through drawing without necessarily using the eyes or direct visualization. Rather, the system employs tactile learning of an input line or shape or graphic, and requires the individual to draw freehand without necessarily using the eyes, the input line or shape.

Figure 1:
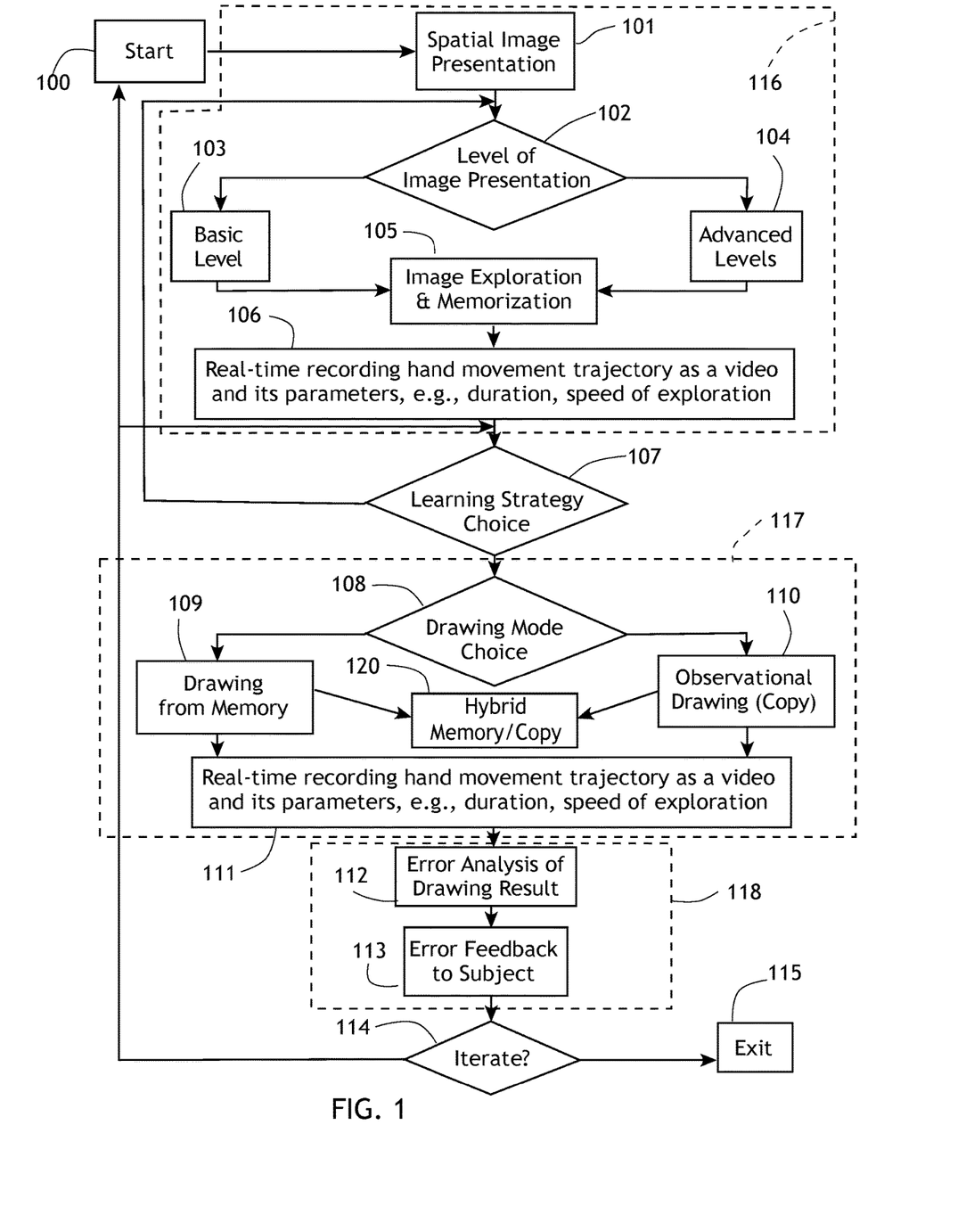
FIG. 1 is a functional block diagram depicting the steps of the method of the invention for training spatial cognition, memory and spatiomotor coordination through drawing.

With regard to FIG. 1, the methodology of the present invention broadly includes three phases that occur sequentially. In an exploration and memorization phase 116, spatial or structural information is presented to an individual, so that an image or spatial structure of a defined conformation is delivered to the subject. Thereafter, the subject is given a time period to memorize the spatial or structural information, with the guidance of descriptive multi-level analysis of the segments or image part under the subject's exploring hand(s) that is provided verbally, electronically or by human trainer simultaneously or sequentially with the exploration. Thereafter, the subject is directed to draw the image or structure that has been conveyed to the subject, with or without contemporaneous perceptual access to the input information. The final phase of the process is to conduct an error analysis 118 of the subject's drawing, in comparison to the input information, and to provide error feedback to the subject for learning and memory correction. This process is preferably reiterated so that the subject carries out repeated presentations of the input line/shape/graphics and experience the kinesthetic action or the visualization of recreating the inputs through drawing, thereby to prompt the subject to create and express graphically the spatial-structural conceptualizations of the input material from memory or otherwise.

More particularly, the process begins at Start 100, followed by the step of spatial image presentation 101 to the subject of the training. The choice of level of image presentation 102 branches to either a basic level 103 (e.g., simple line presentations) or advanced levels 104, such as more complex line drawings, graphics, maps, or the like. At step 105 the subject (trainee) is encouraged to explore the image being presented for a restricted or unrestricted time period, as detailed below, using one of several input methods. Thereafter the subject is allowed to contemplate the image material that has been presented; thereafter the subject is trained to follow a sequence of training principles and multi-level procedures described below. These multi-level analytic procedures aim to train the subject to generalize and apply such analyses themselves to any spatial structure when needed in the future. Externalization by drawing of the internal memory representations generated through the multi-level guided exploration approach of this training method, in particular, forces the enhancement of basic spatial and spatiomotor cognition and memory beyond the enhancement on the drawing task.

At step 107 a learning strategy choice is made, which provides for reiteration of the 116 phase for re-exploration while better satisfied by improving the internal memory image before starting to drawing it, and which also involves the step 108 of drawing choice mode: either drawing solely guided by memory (109), which is the preferred mode for rapid enhancement of spatial memory and cognition, or observational drawing (110), which involves enabling the subject to tactilely explore the image while at the same time drawing the image. A further choice is hybrid memory/copy 111 which combines memory drawing with elements of observational drawing for filling in and correcting local memory gaps.

In the hybrid mode choice 120, the subject starts to perform drawing from memory (i.e., without touching or looking at the original at all), however, if he/she experiences serious memory gaps, he/she is provided access to the original so that he/she can "take a look at"/touch it, but, he/she is instructed to do so only very rarely and briefly; i.e., the original is explored only to fill in some (isolated) memory gaps here and there, and then the subject continues to draw from memory again. This is used very rarely and only at the beginner level, when they may have not memorized it well, and realize their memory-gaps, so they are provided with access to the original as well and are thus allowed to use some perceptual "crutches" to fill in the missing detail in their internal memory image.

During these modes 109, 110, and 120, a real-time recording (step 111) of the subject's hand movements during drawing are recorded, as by touch-screen recording or video recording or the like. After the drawing phase is completed (by subject's indication or by time elapsed, etc.) step 112 requires an error analysis of the drawing, by comparing it to the original spatial image presentation (101). The error analysis can be offered either as an overall evaluation score, performed through preexisting evaluation algorithms, such as bi-dimensional regression, or a recognizability index code, or the like. Or it can be offered as a more training-like, detailed and analytical feedback at several levels, similarly to the multi-level training guidance in the exploration and memorization steps described below.

The error analysis is then communicated (step 113) to the subject, so that the subject may understand the ways in which the drawing comports with or deviates from the original image, and refine, update and stabilize the memory representation in their mind. The error analysis also can be offered either as an overall evaluation score, performed through preexisting evaluation algorithms, such as bi-dimensional regression, or a Recognizability Index code, or the like. Or as a more training-like, detailed and analytical feedback at several levels, similarly to the multi-level training guidance in the exploration and memorization steps described below. The process may then be iterated (step 114), so that the subject may benefit from the error feedback step, or the training session may end at exit step 115.

Figure 2:
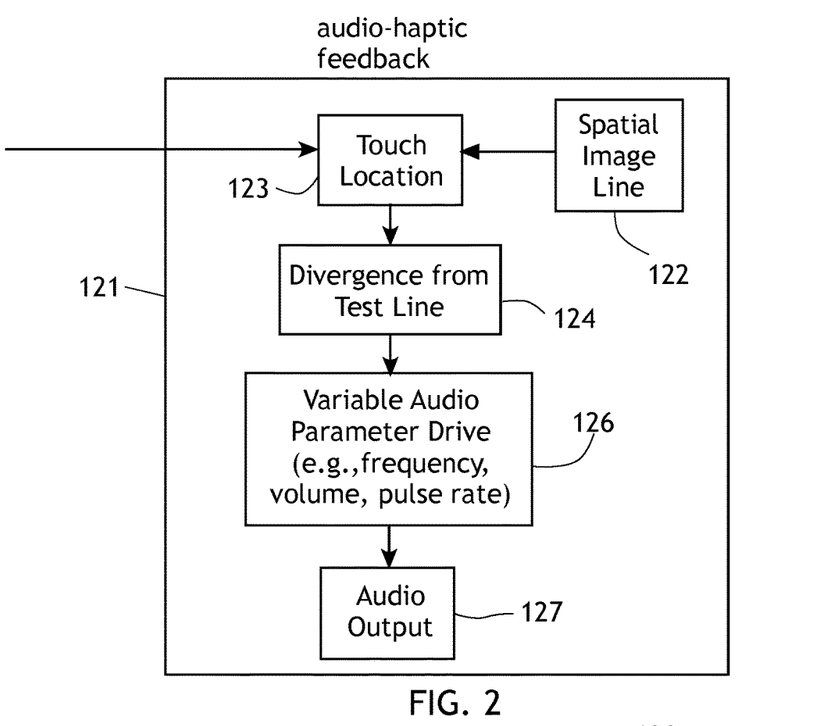
FIG. 2 is a functional block diagram of the method of the invention for audio-haptic feedback for spatial-structure presentation and guidance of haptic exploration system.
Figure 3:
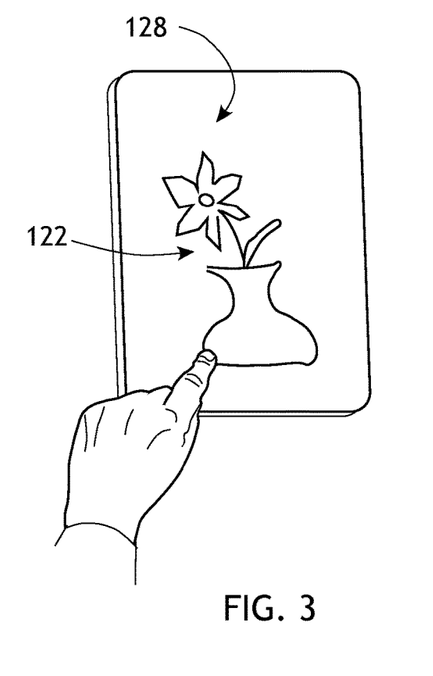
FIG. 3 is a perspective view depicting the image exploration phase of the present invention, carried out on a touch-screen device.

For individuals who are blind or have low visual acuity or are blindfolded, the first phase 116 which includes step 101 of presenting the spatial structural information may be conducted using the novel concept of audio-haptic feedback in conjunction with the exploration and memorization step 105, so that the audio-haptic feedback guides and directs the exploring hand or stylus along the lines or surfaces presenting the spatial structure. With regard to FIG. 2, the audio-haptic feedback step 121 may be carried out using a touch-sensitive screen-based device, such as a tablet-computer, or a telephone screen, or a dedicated device constructed for the methodology of the invention. The individual (training subject) is presented a spatial image 122 designed for training purposes on a touch screen display 128, as depicted in FIG. 3. The training subject cannot visually perceive the image material, and is directed to explore the image using manual touch by placing a finger or stylus on the screen and exploring the surface. Electronic voice or sound may guide the individual to a specific point recommended as a starting point for the exploration of the image. Once the exploration process is initiated, the touch location 123 is compared to line position in the spatial image 122, and the divergence 124 between the two is calculated in real time. The magnitude of the divergence is employed to control a variable audio parameter drive 126, which varies a characteristic of an audio output signal 127 that is delivered to the training subject. For example, the frequency of the audio output may be varied in proportion to the magnitude of the divergence to apprise the subject of the distance from the finger touch to an image line. Likewise, the volume or timbre of the audio output may be varied in the same manner, or a pulsed audio output may be modified in pulse rate to indicate the divergence of the touch from the line. More than one of these characteristics may be varied together to present a more robust feedback signal to the subject. The variations in the audio output are used to haptically explore and follow the line even without any vision, guided by the sound being produced when the touch is on the line but which varies rapidly or diminishes with a gradient when the touch departs from the line. The subject may quickly acquire the skill to scan the spatial image material, follow one or more lines, or the like, to learn the nature or shape of the spatial image.

Figure 6:
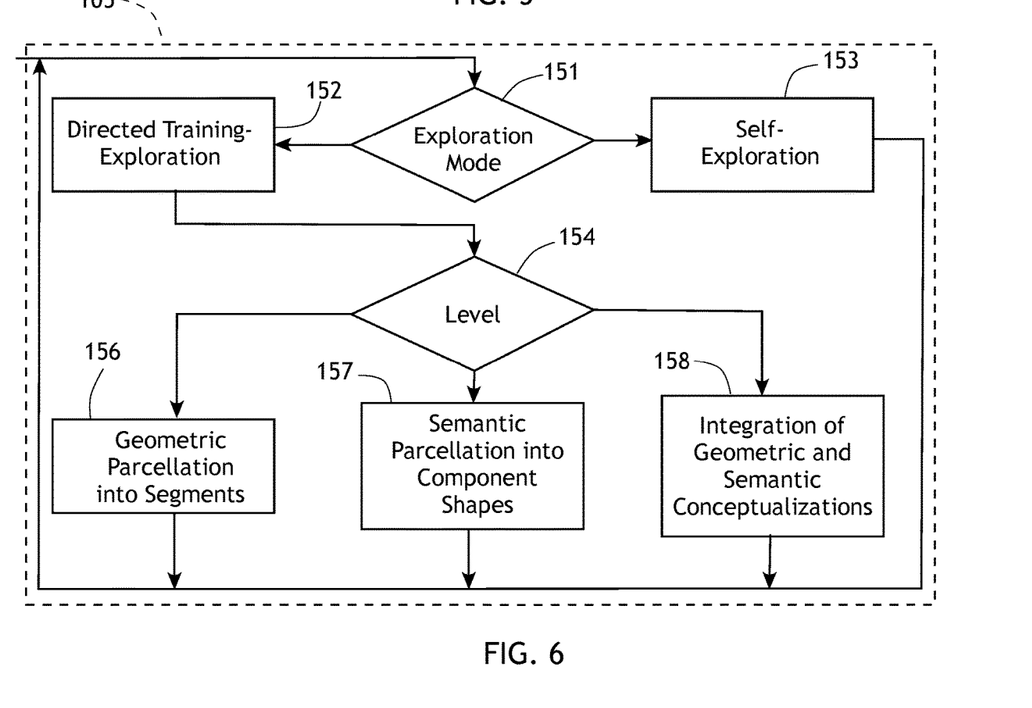
FIG. 6 is a functional block diagram depicting the image exploration and memorization phase of the training method of the invention.

With regard to FIG. 6, the image exploration and memorization step 105 of FIG. 1 is comprised first of step 151, in which the exploration mode is chosen, either directed training exploration 152 or self-exploration 153. The directed training level is selected at step 154, including geometric parcellation of the image into segments (156), semantic parcellation into component shapes (157), and integration of the geometric and semantic conceptualizations (158). These steps may be carried out by voiced directions or textual presentations. Geometric parcellation involves directing the subject to analyze the image material to identify inflection points, determine and describe spatial characteristics, both absolute and relative to adjacent segments, then segment-by-segment evaluation of line features, such as segment orientation, length (absolute, i.e., in relation to the length of the original segment, or relative—with respect to the neighboring segments in the performed drawing), angular relationships, curvature, and the like. These tasks encourage the subject to undertake a geometric spatial analysis of image structure, guiding attention to both detailed characteristics of elements and their spatial relationships, and throughout the training across a multitude of spatial configurations, images, graphics, maps, and the like, to generalize these analytic principles and become able to apply them independently to new material.

The semantic parcellation step 157 directs the subject to think beyond the geometric relationships of the image material, and identify the morphology and meaning of the image material. For example, if the image lines define a tree shape, or a human face, these factors are presented to the subject, and the familiar elements of these shaped may be elucidated; i.e., the trunk, roots, branches, and leaves of a tree may be examined in detail, or, for a facial image, the eyes, nose, mouth, chin, ears, and the like may be pointed out and examined. These semantic factors serve to further reinforce the subject's "mental map" of the image material, which aids in the subsequent drawing-from-memory task. As with geometric parcellation, by going through this step throughout the training across a multitude of spatial configurations, images, graphics, maps, and the like, the subject is enabled to generalize these analytic principles of exploration and become able to apply them independently to new material.

The integration step 158 combines the teachings of the geometric parcellation 156 and semantic parcellation 157, either following those steps sequentially or by introducing both conceptualizations in an interwoven presentation. This step augments the mental reconstruction in memory of the connected global spatial architecture of the image material, with emphasis on the nature of the transitions between geometric segments and their relationships to the identifiable portions of the semantic elements of the image.

The self-exploration mode 153 allows the subject to delve into the image material using the subject's native understanding of images and spatial organization. This mode may be useful to establish a baseline for a subject, or may be used for a subject who has already undergone the geometric, semantic or integration steps of previous iterations of the training protocol.

Figure 4:
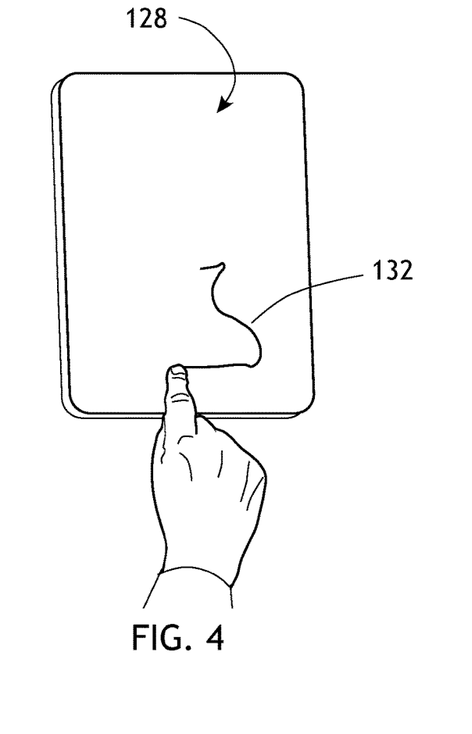
FIG. 4 is a perspective view depicting the drawing phase of the present invention, carried out on a touch-screen device.

In the next phase, depicted in FIG. 4, the subject reproduces drawing image 122 manually, using a finger or touch stylus or a mouse or the like guided solely by the image formed in memory from the previous exploration and memorization phase, thus producing his/her own drawing 132. Subsequently, the subject has the option to explore his/her own (imperfect) drawing 132 represented on the tablet screen 128 as a self-evaluation or advanced error feedback. Here again the audio-haptic system of the invention may be employed to automate this step and apprise the subject of discrepancies between the drawing and the input.

Figure 7:
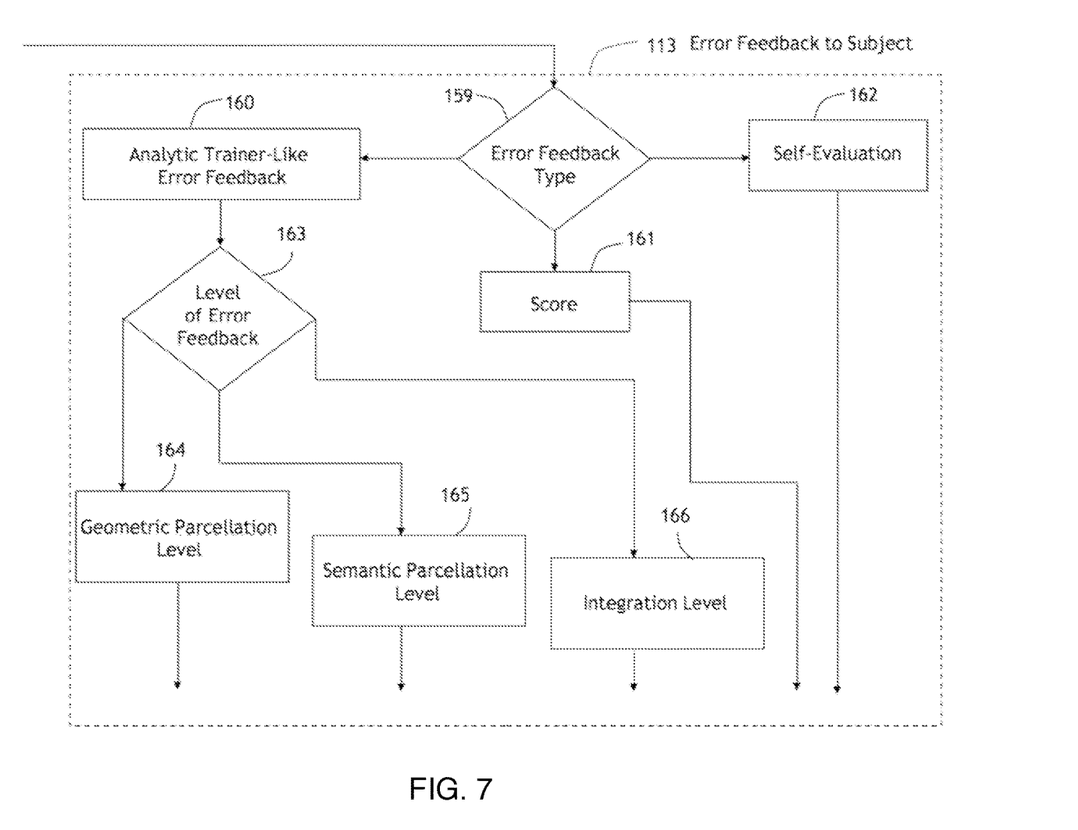
FIG. 7 is a function block diagram depicting the error feedback phase of the training method of the invention.

In the final phase, depicted in FIG. 7, the error feedback step 113 of FIG. 1 is comprised first of step 159, in which the error feedback type is chosen, either analytic trainer-like error feedback 160 or score type feedback 161 or self-evaluation 162, which may be based on self-exploration of the subject's own drawing through applying the training principles at geometric, or at semantic, or at plurality of analytical levels of exploration and evaluation, learned during the preceding training steps. The specific type of trainer-like error feedback is selected at step 163, including selection of a type of feedback operating at the level of segments from the geometric parcellation of the image (164), or at the level of image parts from the semantic parcellation into component parts (165), or at the level of errors at the integration of the geometric and semantic conceptualizations into the complete image architecture (166). These steps may be carried out by voiced directions or textual presentations initiated electronically when the respective segment in step 164, or image part in 165 etc of the evaluated drawing are being touched.

The advanced error feedback is provided by computerized voice feedback, based on computer analysis of the errors in drawing 132 in the form of an overall score 161 or a set of scores along several general characteristics of the drawn image 161 as an output from a computer program/code calculating the errors 124 in the drawing such as errors in the position, orientation, size, etc of the lines of the drawing relative to those of the object structure information provided to the subject; or in the form of more, trainer-like, detailed and instructive feedback 160 based on the computational error analysis and evaluation of drawing 132 at each of the training levels and principles used in the phase of Image Exploration and Memorization, such as at each of said levels of analysis of geometric segments, or semantic parts or plurality analysis; this detailed analytical feedback, segment by segment and/or part-by-part along the full drawing trajectory is a major component of the training process. The geometric level error feedback may include information about the deviations from geometric characteristics of the drawing-segment being touched, or transitions between segments and respective spatial relationships and the like. The semantic level error feedback may include information about about the deviations from semantic characteristics of the meaningful drawing-part being touched, or transitions between parts, and the respective spatial relationships. The integration level error feedback may include information about a plurality of aspects of different level analyses within the context of their integration into the global spatial image. This multi-level error feedback thus provides error information to be used by the subject to correct errors in memory and precise motor control of the hand. The audio-haptic feature described previously allows the real-time automation of the error feedback step 118.

The same process can be fully applied to any other manner of presenting spatial structure information on a tablet, computer, cellphone, or any other electronic device, using any form of electrostatic, vibrational, electronic-tactile image rendering, or a plurality of such in case they provide sufficient resolution such as being pixel-wise The image representation drawing made by the subject is made either by finger or by moving a stylus or a cursor, etc. across the surface of the tablet screen, and the feedback is provided by an automated computer algorithm installed as an app in the tablet, that is designed to analyze automatically the specified discrepancies in the drawing generated by the subject and convey them in step 113 to the subject in computer-generated voice instructions or otherwise, in a hierarchical sequence similar to that of the trainer of the previous embodiment, including feedback and instructions based on the geometric, semantic or a plurality of training principles. Also, during the hierarchical trainer-like error feedback, they are provided with options to explore either the original or their own drawing through audio-haptic or other method, so that they can hear the respective feedback about the geometric or semantic characteristics or plurality of characteristics of a particular segment or image part or transitions/connections between these segments/parts/etc., prompted by simultaneously touching the respective segment, part, transition section, etc of the spatial image or the drawn image representation.

Figure 5:
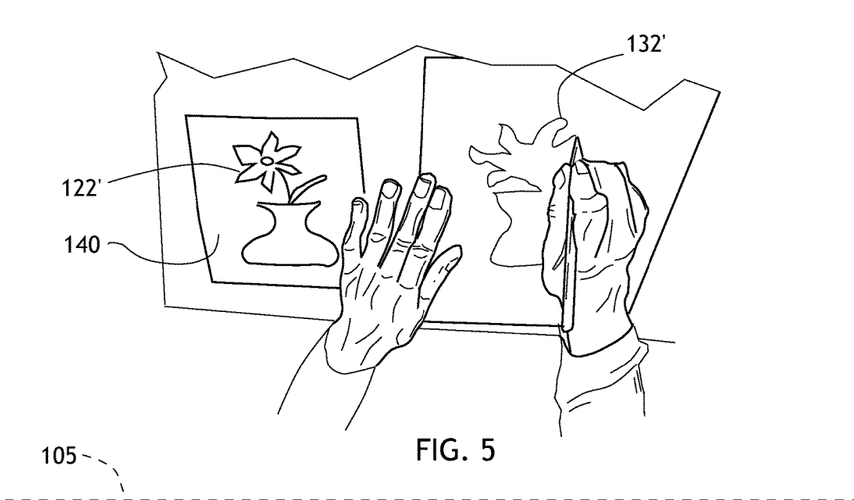
FIG. 5 is a perspective view of a further embodiment of the invention in which the methodology for training spatial cognition, memory and spatiomotor coordination through drawing is carried out without resort to a touch-screen device.

With regard to FIG. 5, another embodiment of the invention uses a uni-sensory means of conveying the drawing structure to the subject, such as a raised-line drawing 122' made on a commercially-available thermal plastic sheet or 'swelling paper' 140, in which heating the plastic raises the drawn lines a millimeter or two up from the rest of the surface, so that they may be felt by tactile-haptic exploration of the plastic sheet with a moving fingertip for the subject to gain a detailed impression of the drawing layout by repeated exploration of the image. The term 'tactile-haptic' refers to the combined information from touch on the skin and the positioning of the limbs and fingers to provide the information about the image structure as the fingertip is moved along the lines of the drawing. The first stage of the procedure is under trainer observation and provision of feedback and guidance at an appropriate level for the subject to repeat reiterate this phase of exploration and memorization until a clear mental image of the drawing structure is developed. Importantly, uninstructed repetition by itself cannot help them; for example, congenitally blind have been using tactile perception actively all their life, but they are typically not better at all in "seeing" in detail and memorizing properly such detailed drawings, as well as not able at all to coordinate and guide their hand solely from memory to make any recognizable drawing before the training.

The second stage of the procedure is then for the subject to make a drawing of the memorized structure on paper or a touch screen, which is then critiqued by a trainer, who provides feedback about any discrepancies in the drawing at the appropriate level or a sequence of the above levels throughout the drawing iterations. The discrepancies may include the overall scale of the drawing, or other global shape distortions, the omission of notable features, the strategy of sequencing the various lines in the drawing, the positioning of the pen after being lifted from the paper, the shapes of local features, analyses in geometric or semantic nature, strategies for global and local attention, and so on. The procedure is then iterated until a satisfactory result is obtained.

The third stage of the training procedure is to repeat the first and second stages with a set of different drawings, so that the subject learns to generalize the learning principles and procedure across a range of different drawing structures and progressively improves the ability to form accurate spatial memory and produce accurate readout of that memory in the form of drawing, as well as improves the precise spatio-motor control under mental-image guidance.

The drawing mode choice 108 also includes the observational drawing mode 110, in which the subject uses one hand to explore and trace the lines of the spatial image input, while the subject draws the perceived image content with the other hand. Although this mode does not involve the demanding spatial-memory-guided activity described previously, it does utilize and enhance subject's spatial recognition, attention and internal mapping abilities to some degree, and may serve as an enter to introduce the deeper involvement of the drawing-from-memory mode 109.

The foregoing description of the preferred embodiments of the invention has been presented for purposes of illustration and description. It is not intended to be exhaustive or to limit the invention to the precise form disclosed, and many modifications and variations are possible in light of the above training without deviating from the spirit and the scope of the invention. The embodiments described are selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

The invention claimed is:

1. A method for improving a subject's spatial cognition and spatial memory, including:
   presenting spatial image information to the person through a non-visual medium; non-visual exploration and memorization of the spatial image to enhance the subject's understanding of the nature and relationships of components of the spatial image information to promote augmentation of the subject's spatial image memory;
   the subject thereafter drawing an image representation of the spatial image information;
   detecting and encoding errors in the image representation relative to the original spatial image; and,
   providing interactive feedback to the subject based on the subject's image representation
   wherein the step of providing interactive feedback includes identifying discrepancies between the explored spatial image information and the drawn image representation. including at least one of a group of factors including: the overall scale of the drawing, global shape distortions, the omission of notable features, the strategy of sequencing the various lines in the drawing the re-positioning of the drawing touch after being lifted from the drawing surface. the shapes of local image features, analyses in geometric or semantic nature. and strategies for global and local attention.

2. The method of claim 1, wherein the step of image exploration and memorization includes geometric parcellation of the spatial image information to direct attention to geometric relationships of components of the spatial image information.

3. The method of claim 1, wherein said step of image exploration and memorization includes semantic parcellation of the spatial image information to examine semantic relationships of components of the spatial image information.

4. The method of claim 3, wherein said step of semantic parcellation includes directing the subject to identify the morphology and image-wise identity of components of the spatial image information, including deconstructing the image-wise component into commonly identifiable elements.

5. The method of claim 4, further including geometric parcellation of the spatial image information, including directing the subject to analyze the spatial image information by at least one of the following tasks: identify line segments, identify in flection points, determine and describe spatial characteristics, both absolute and relative to adjacent line segments, segment-by-segment evaluation of line features, including segment orientation, length, angular relationships of segments, and curvature of line segments.

6. The method of claim 5, wherein said step of image parcellation includes integration of its subcomponents of geometric and semantic parcellation in an interwoven sequence of steps.

7. The method of claim 1, wherein the step of presenting spatial image information includes providing a tangible sheet of material with raised lines representing the lines in a line drawing, said raised lines being perceptible by finger touch.

8. The method of claim 1, wherein the step of presenting spatial image information includes providing a set of three-dimensional solid or wire-frame objects that portray the spatial image information.

9. The method of claim 1, further including the step of recording the hand movements of the subject's hand while carrying out the image exploration and memorization step using a recording device driven by the position of an exploratory tool [stylus, mouse, finger, keyboard] operated by the subject's hand.

10. The method of claim 1, further including the step of recording the hand movements of the subject's hand while the subject draws the image representation, using a recording device driven by the position of a drawing tool [stylus, mouse, finger, keyboard] operated by the subject's hand.

11. The method of claim 1, wherein the step of drawing the image representation is carried out by the subject while the subject is given tactile access to the spatial image information.

12. The method of claim 1,
wherein said interactive feedback step includes generating an audio-haptic feedback signal to annunciate said discrepancies between the explored spatial image information and the drawn image representation.

13. The method of claim 12, wherein said audio-haptic feedback signal is varied by altering an audio characteristic in response to said discrepancies, said audio characteristic being at least one of: audio frequency, amplitude, timbre and pulse rate.

14. The method of claim 12, wherein said audio-haptic feedback signal is provided through an electronic voice for delivering to the subject descriptive multi-level analysis of the segments or image parts or the image as a whole under the exploring hand(s) of the subject.

15. The method of claim 12, further including the step of displaying said image representation, and using said audio-haptic feedback signal to either annunciate said errors in said image representation, and/or to provide guidance and learning strategy recommendations to the subject during said interactive feedback step.

* * * * *